United States Patent [19]

Fleischle

[11] Plant 4,528

[45] Apr. 29, 1980

[54] DISTINCT VARIETY OF STREPTOCARPUS NAMED FREDA

[75] Inventor: Gerhard Fleischle, Vaihingen, Fed. Rep. of Germany

[73] Assignee: Oglevee Associates, Inc., Connellsville, Pa.

[21] Appl. No.: 958,807

[22] Filed: Nov. 8, 1978

[51] Int. Cl.[2] ..... A01H 5/00

[52] U.S. Cl. ..... Plt./68

[58] Field of Search ..... Plt./68

*Primary Examiner*—Robert E. Bagwill
*Assistant Examiner*—James R. Feyrer
*Attorney, Agent, or Firm*—Webb, Burden, Robinson & Webb

[57] ABSTRACT

A new variety of Streptocarpus plant is characterized by its beet purple flower having a yellow throat. It has large flowers, long permanence and is generally nonfertile.

1 Drawing Figure

BACKGROUND OF THE NEW PLANT

The present invention comprises a new and distinct cultivar of *Streptocarpus* × *hybridus* known by the varietal name of Freda, formerly named Gloria Rot. The new cultivar is an irradiated sport of a Streptocarpus known by the varietal name of Gloria Rosa. The new cultivar is distinguished from Gloria Rosa by the difference in color and a shorter response time by one week. In addition, the flowers of Freda are larger than the flowers of Gloria Rosa.

The new cultivar was discovered in 1977 in Vaihingen, Federal Republic of Germany; was first asexually reproduced by cuttings in Vaihingen, Federal Republic of Germany; and has been repeatedly asexually reproduced by cuttings at Oglevee Floral Company in Connellsville, Pa. It has been found to retain its distinctive characteristics through successive propagations.

The new cultivar, when grown in a greenhouse in Connellsville, Pa., has a response time of nine weeks. This response time is measured from a plantlet which is a well rooted young plant in a five centimeter pot to a flowering plant in a ten centimeter pot.

DESCRIPTION OF THE DRAWING

The accompanying drawing illustrates the new cultivar, the color being as nearly true as possible with color illustrations of this type.

DESCRIPTION OF THE NEW PLANT

The following detailed description sets forth the characteristics of the new cultivar. The data which defines these characteristics were collected from asexual reproductions carried out by the Oglevee Floral Company in Connellsville, Pa. The plant history was taken on eight week plants blossomed under natural light in a greenhouse and color readings were taken indoors under 100 foot candles of cool white fluorescent light. Color references are primarily to the R.H.S. color chart of the Royal Horticultural Society of London. Some color reference is to Exotica III and such reference is duly noted.

Botanical classification: Gesneriaceae (Family); *Streptocarpus* × *hybridus* (Genus × species).

Flower:

*Fully expanded.*—Six and one-half centimeters.

*Borne.*—In clusters of one to six flowers per flower stalk above the foliage. Flower stalks arise from mid-rib of each leaf.

*Stems.*—Single, long and pubescent with some stems being flat shaped rather than round.

*Form.*—Funnel formed in an umbel.

*Permanence.*—Long lasting 21 to 25 days.

*Color*

Front of petals.—Fan 2, Red Purple Group 61-A.

Throat.—Fan 1, Yellow Green Group 154-B.

Base of petals.—Fan 2, Red Purple Group 69-C.

Reverse of petals.—Fan 2, Red Purple Group 74-D.

Tonality from a distance.—Predominantly beet purple with yellow throat (Exotica III).

Discoloration.—Insignificant.

Petals:

*Texture.*—Velvet.

*Appearance.*—Individually lobed with slightly serrated margin.

*Arrangement.*—Regularly united into an elliptical form.

*Persistence.*—Lives for 21 to 25 days and remains on plant in dry form until picked.

*Fragrance.*—None.

Reproductive organs:

*Anthers.*—Two per flower and interconnected.

*Filament.*—Two and one-half centimeters initiating from the base of petal and extending to the anther.

*Pollen.*—Generally nonfertile.

*Style.*—Extends from tip of ovary one centimeter and terminates in a flattened stigma.

*Ovaries.*—Long and narrow, one and one-half centimeters long and two millimeters in diameter.

Plant:

*Form.*—Leaves rosulete from a crown at the soil line.

*Growth.*—A spreading, free flowing habit with leaves being elliptic.

*Height from soil line.*—15 to 20 centimeters.

*Spread.*—25 to 30 centimeters.

Foliage:

*Top side.*—Fan 3 Green Group 137-B.

*Size.*—10 to 18 centimeters in length and 7 to 10 centimeters wide at the widest point.

*Quantity.*—Four to seven leaves.

*Shape.*—Elliptic.
*Ribs and veins.*—Pinnate.
*Rib and vein color.*—Fan 3 Green Group 139-D.
*Underside.*—Fan 4 Greyed Green Group 193-A.
*Stipules.*—None.

I claim:

1. A new and distinct variety of Streptocarpus substantially as herein shown and described.

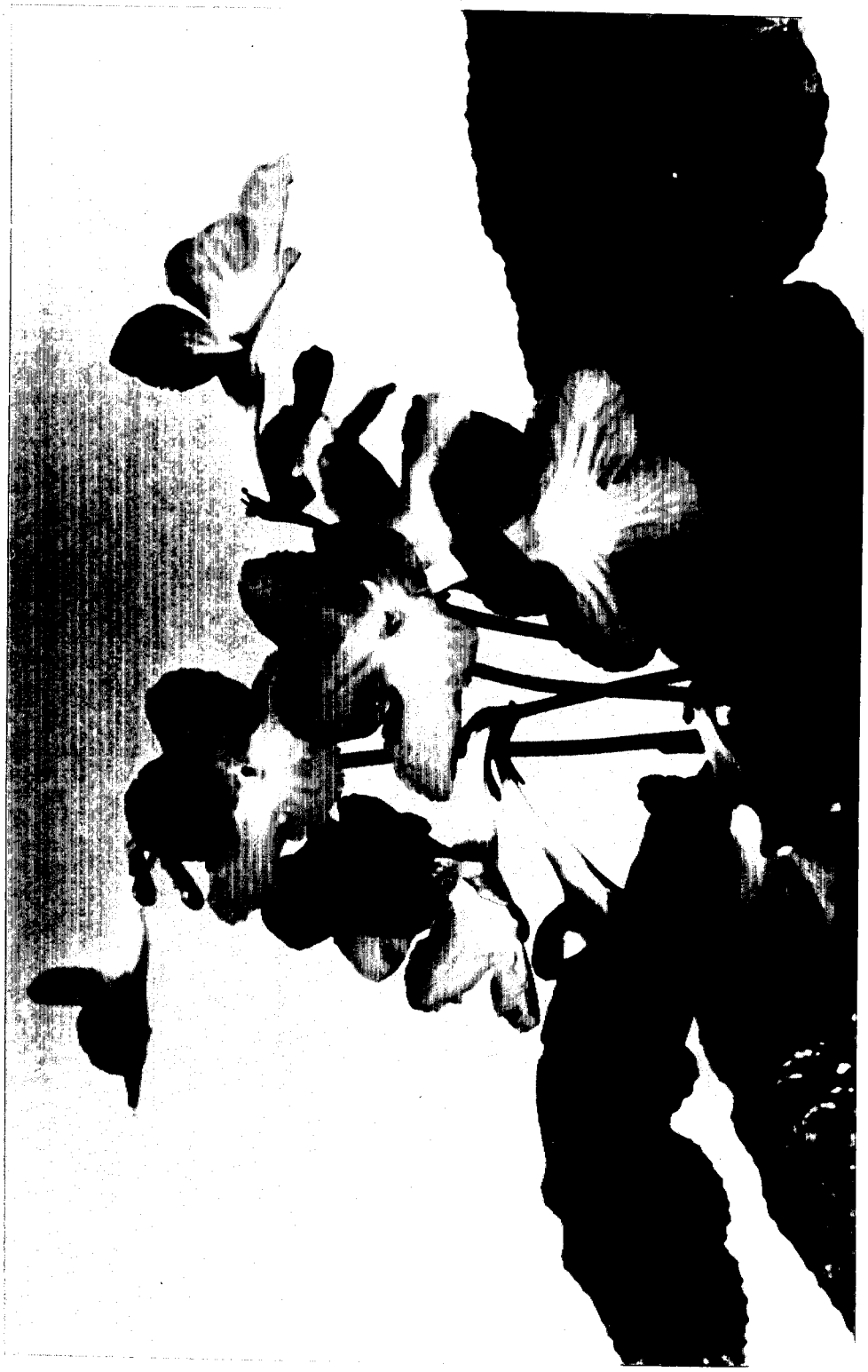

* * * * *